Figure 1:
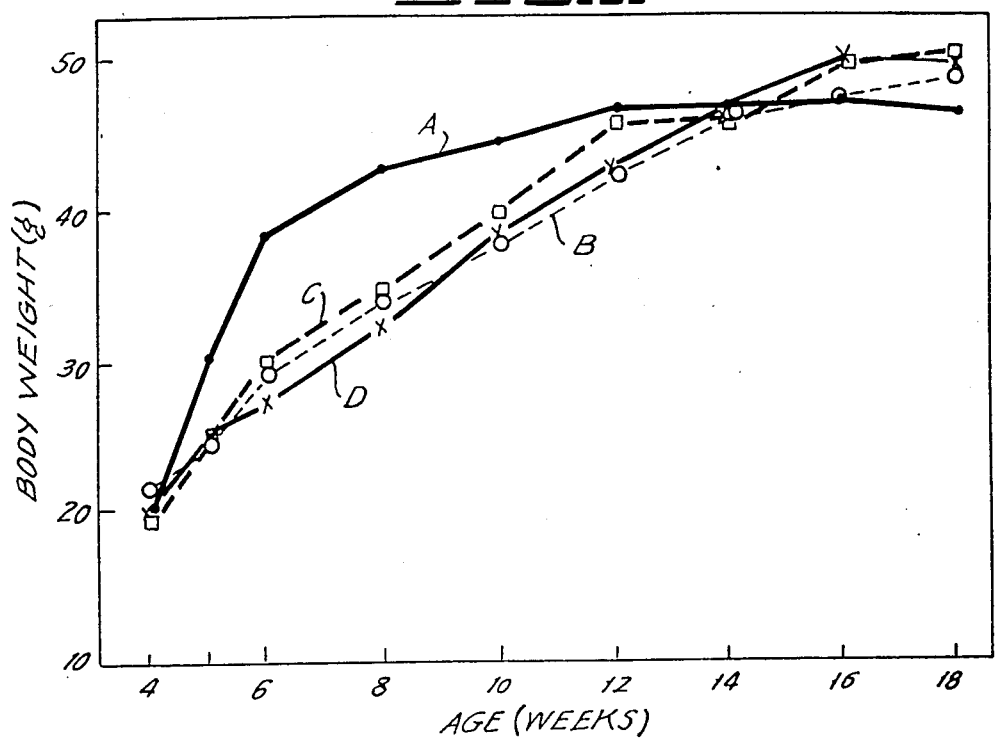

United States Patent [19]

Coleman et al.

[11] Patent Number: 4,666,898
[45] Date of Patent: May 19, 1987

[54] TREATMENT OF OBESITY, DIABETES AND OTHER SYMPTOMS OF HYPERCORTICOIDISM USING ETIOCHOLANOLONES

[75] Inventors: Douglas L. Coleman, Seal Harbor, Me.; Norman Applezweig, New York, N.Y.

[73] Assignees: Jackson Lab., Bar Harbor, Me.; Progenics, Inc., New York, N.Y.

[21] Appl. No.: 683,423

[22] Filed: Dec. 19, 1984

Related U.S. Application Data

[63] Continuation-in-part of Ser. No. 566,223, Dec. 28, 1983, abandoned.

[51] Int. Cl.$^4$ .............................................. A61K 31/56
[52] U.S. Cl. ..................... 514/177; 514/866; 514/909
[58] Field of Search ........................................ 514/177

[56] References Cited

U.S. PATENT DOCUMENTS 4,507,289  3/1985  Coleman et al. ..................... 514/170
4,518,595  5/1985  Coleman et al. ..................... 514/178

OTHER PUBLICATIONS

Fieser et al., "Steroids", (1959), p. 507 relied on.
Merck Index, (1976), Ninth Edition, Par. 676, p. 87 relied on.
"Steroids" by Fieser et al., pp. 504–505, (1959).
Louis F. Fieser and Mary Fieser, "Steroids", (1959), p. 506.
Douglas L. Coleman, "Antiobesity Effects of Etiocholanolones in Diabetes (db), Viable Yellow ($A^{vy}$), and Normal Mice*", Endocrinology, vol. 117, No. 6, pp. 2279–2283.
D. L. Coleman, E. H. Leiter and N. Applezweig, "Therapeutic Effects of Dehydroepiandrosterone Metabolites in Diabetes Mutant Mice", Endocrinology, vol. 115, No. 1, pp. 239–243.

Primary Examiner—Leonard Schenkman
Assistant Examiner—Joseph A. Lipovsky
Attorney, Agent, or Firm—Ostrolenk, Faber, Gerb & Soffen

[57] ABSTRACT

Obesity, diabetes obesity syndromes and associated hypercorticoidism are treated with $\alpha$ and/or $\beta$-etiocholanolone.

25 Claims, 4 Drawing Figures

TREATMENT OF OBESITY, DIABETES AND OTHER SYMPTOMS OF HYPERCORTICOIDISM USING ETIOCHOLANOLONES

CROSS-REFERENCE TO RELATED APPLICATION

This is a continuation-in-part of U.S. patent application Ser. No. 566,223, filed Dec. 28, 1983, now abandoned. This invention is related to U.S. patent application Ser. No. 515,354, filed by the present inventors on July 19, 1983 for "Method for Treating Diabetes Using DHEA Components" and the contents of that application (now U.S. Pat. No. 4,518,595) are incorporated herein by reference.

BACKGROUND OF THE INVENTION

The major function of the adrenal gland is to regulate metabolism in the body so that an intermittent intake of food can be regulated to maintain a constant metabolite supply to the cells. This is accomplished by producing steroid hormones which can control the conversion of incoming nutrients, such as aminoacids, glucose and fats into storage depots from which they can thereafter be released or interchanged, allowing a continuous flow of optimum energy and growth factors to the cells.

The steroid hormones are divided mainly into three classes. The first is glucocorticoids (cortisol), also known as gluconeogenic or diabetogenic steriods, which can convert aminoacids into glucose for direct use or store the glucose as glycogen for later use. Cortisol can therefore have an anti-anabolic effect through the depletion of aminoacids needed for protein synthesis and a diabetogenic effect through the direct release of glucose from the glycogen store.

A glucocorticoid excess, resulting from an excess of the pituitary hormone, adrenal cortico-trophic hormone (ACTH), which controls cortisol production, causes Cushing's Syndrome, an uncommon disease. Intake of an excess amount of cortisol from pharmacological use of steroids can also cause Cushing's Syndrome or Cushingoid-like disorders (hypercorticosteroidism, or more briefly hypercorticoidism) which are progeric in that they resemble the symptoms of the diseases of aging, e.g. obesity, hypertension, diabetes, renal stones, osteoporosis, mental disorder, menstrual disturbance, susceptibility to infection and poor wound healing.

The second category of steroids is known as the adrenal androgens. Dehydroepiandrosterone (DHEA) is the principal representative of this category. The adrenal androgens which have an anabolic action are produced with puberty, reach a peak in early adulthood and then, beyond the age of 50, decline to very low levels. Secretion of ACTH, which also controls corticosteroid production, shows no such age related fluctuation.

The third category of adrenal steroids is the mineralocorticoids (aldosterone) which control the mineral balance of the body and is partially under ACTH control in that ACTH accelerates the conversion of cholesterol to all adrenal steroids.

When the body is subjected to stress, physical or mental, e.g. injury, cold, starvation or threats, real or imagined, ACTH stimulates the adrenal cortex to produce steroids in increased amounts in order to provide the body with resources necessary for response to the stress, storage or release of glucose when needed, lipid deposition or mobilization in order to maintain the energy equilibrium of the body under conditions where extra energy may be needed and/or starvation of the cells becomes a possibility.

Under normal conditions, ACTH stimulates the adrenals to secrete both cortisol and DHEA. In the aging individual, cortisol is stimulated but DHEA is not, thus resulting in relative hypercortisolism.

It is shown in the aforesaid related application that DHEA is useful in the treatment of diabetes in mutant mice and treatment of adult-onset diabetes in obese individuals. The genetic form of diabetes in mice is associated with hypercorticosteroidism. Hypercorticosteroid syndromes can occur as a result of excessive ACTH production due either to stress, hypofunction of the adrenal glands, pituitary tumors, ectopic ACTH production or administration of pharmacologic doses of cortisol. DHEA is also known to be useful as an anti-obesity agent in animals and humans. Yen et al, Prevention of Obesity in Avy/a Mice by Dehydroepiandrosterone, Lipids, 12(5), 409 (1977); Kritchevsky et al, Influence of Dehydroepiandrosterone (DHEA) Cholesterol Metabolism in Rats, Pharm. Res. Comm., 15, No. 9 (1983); Abrahamsson et al, Catabolic Effects and the Influence on Horomonal Variables under Treatment with Gynodian-Depot or Dehydroepiandrosterone (DHEA) Oenanthate, Maturitas, 3 (1981) 225–234.

DHEA is metabolized in the body. A major metabolite is etiocholanolone (5-$\beta$-androstan-3-$\alpha$-ol-17-one, (hereinafter referred to as $\alpha$-ET) and in normal individuals it is excreted in amounts of about 0.5 mg/100 ml. $\beta$-etiocholanolone (5-$\beta$-androstan-3-$\beta$-ol-17-one, hereinafter referred to as $\beta$-ET), was reported to be a minor metabolite of DHEA although evidence for its presence was based upon unmeasured spots on chromatograph strips observed during measurements of etiocholanolone excretion. Even when large quantities of $\beta$-ET are ingested, most of the recovered excretion product is in the form of $\alpha$-ET, with less than 5% of $\beta$-ET found. Kappas, et al, *The Thermogenic Effect and Metabolite Fate of Etiocholanolone in Man*, J. Clin. Endocrin. & Metab., 18, 1043–1055 (1958). It thus appears that the 3$\beta$-hydroxy compound undergoes almost quantitative conversion to the 3-$\alpha$-hydroxy compound suggesting that the 3-$\beta$-ET is not a natural compound but may be an artifact of isolation.

To confirm that $\beta$-ET is not of natural origin, we used an RIA method for $\alpha$-ET which is far more sensitive than existing chromatographic techniques and found that the injection in man of 40 mg of $\beta$-ET yielded a serum value for etiocholanolone equal to that obtained from 40 mg of injected etiocholanolone. The antiserum used had insiginficant cross-reactivity with unchanged $\beta$-ET.

It is considered that variations in response between the $\alpha$ and $\beta$ compounds are due to differences in the concentration of etiocholanolone available in the serum as the conversion from $\beta$ to $\alpha$ takes place. The conversion time could also account for differences in sojurn time, excretion rate and bioavailability of the two compounds and therefore different interactions with receptors and responses of target organs.

While we have shown that both $\alpha$- and $\beta$-ET are effective in preventing hyperglycemia and excess fat accumulation, the rates at which these actions take place may be influenced by the bioavailability of one or another of the isomers; the $\beta$-ET serving as a slow delivery system with more prolonged action and the $\alpha$-ET as a more rapid but shorter-acting agent. In the diabetic animal, a more prolonged effect may be optimum whereas in the obese animal, a higher initial quantity of etiocholanalone may be desirable. Our results indicate that this is so; α-ET is more effective in the obese animal, while β-ET is more effective than α-ET in the diabetic.

α-ET had been considered to be an inert end product whose sole fate was conjugation and excretion until it was shown that in its free (unconjugated) state, it had highly potent pyrogenic effects when injected intramuscularly in males, less potency in females and none in other species. No febrile reaction results when α-ET is administered intravenosly, or orally, or when β-ET is administered by any route. Kappas, et al., *Thermogenic Properties of Steroids, in Methods in Hormone Research,* Dorfman Ed. Vol. 4, p. 1 (New York & London Academic Press) (1965).

The spectrum of biological significance for etiocholanolones has been extended to include the regulation of porphyrin and hemesynthesis in hepatic and erythroid cells. Granick et al., *Steroid Control of Porphyrin and Hemebiosynthesis, A New Biological Function of Steroid Hormone Metabolites,* Proc. Nat. Acad. Sci., 57:1463 (1967). α-ET as well as other non-pyrogenic 5-β saturated steroids are also inducers of porphyrin synthesis. Wolff, et al., *The Biological Properties of Etiocholanolone,* Ann. Int. Med., 67, 1268–1295 (1967).

It has now been discovered that the administration of α-ET, β-ET or mixtures thereof reproduce the effects of DHEA in preventing the development of hyperglycemia and diabetes possibly by antagonizing the effects of hypercorticoidism. It was also discovered that the effective therapeutic amounts of these compounds are considerably lower than the dosage of DHEA required for maximum effect in normalizing blood sugar and maintaining islet integrity. It has further been found that these compounds are superior anti-obesity agents compared to DHEA.

It is accordingly the object of this invention to provide a new method for treating obesity, diabetes-obesity syndrome and associated hypercorticoidism and enhancing the function or by preventing the destruction of the pancreatic islet beta cells using α-ET and/or β-ET as anti-obesity antidiabetic and antihyperglycemic agents.

Figure 2:
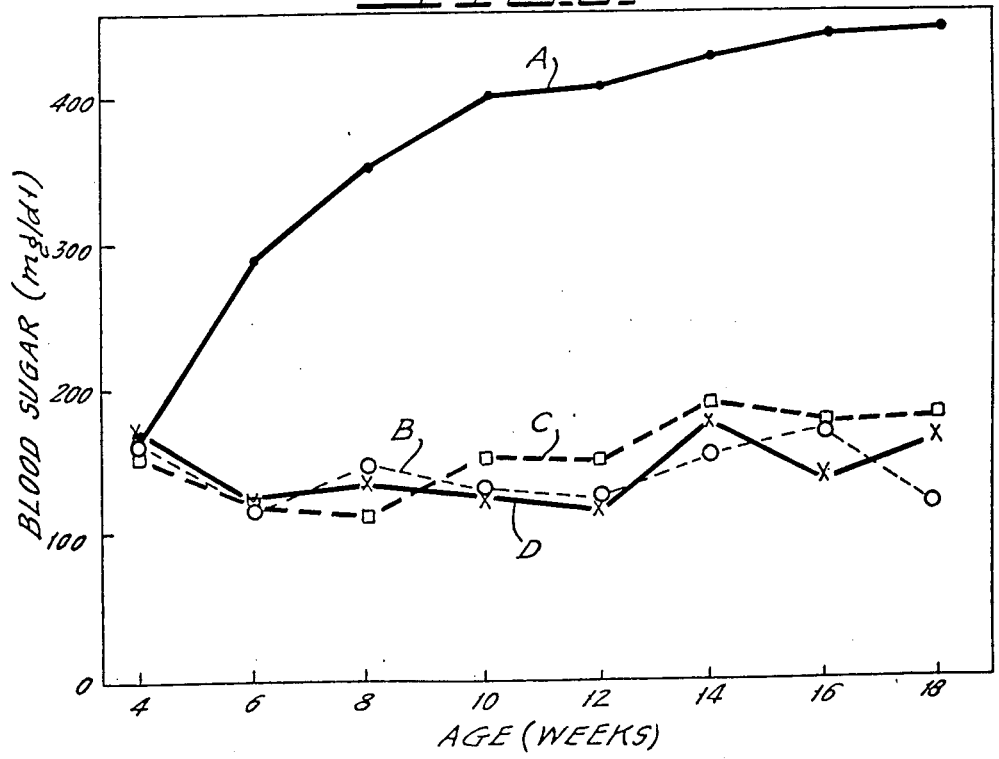
Figure 3:
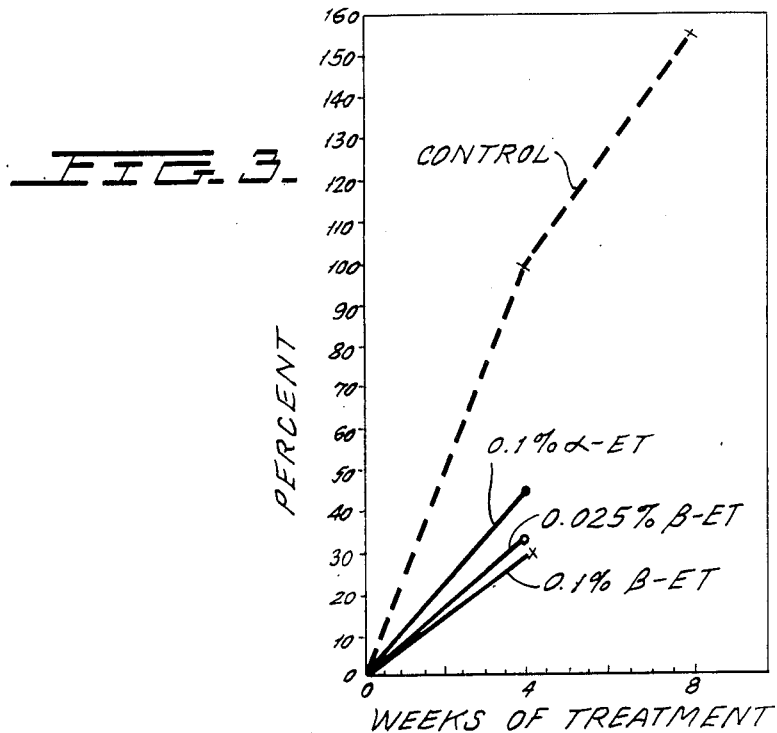

This and other objects of the invention will become apparent to those skilled in this art from the following description in which:

FIG. 1 charts weight gain of tested diabeticobese mice;

FIG. 2 charts the blood sugar of the diabeticobese mice;

FIG. 3 charts weight gain of Avy/a mice; and

Figure 4:
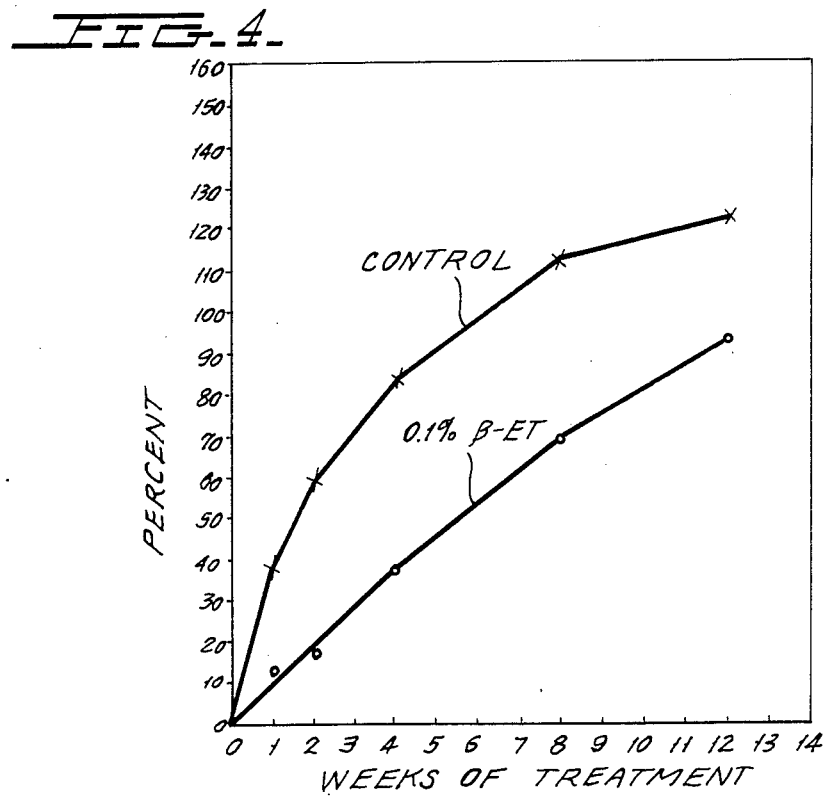

FIG. 4 charts weight gain of C57BL/6J mice.

SUMMARY OF THE INVENTION

This invention relates to the treatment of obesity, diabetes-obesity syndromes and resulting hypercorticoidism through the administration of α-ET and/or β-ET and to enhancement of the function of the pancreatic islet beta cells.

DESCRIPTION OF THE INVENTION

In accordance with the present invention, α-ET and/or β-ET is administered to an individual in order to treat various hyperactivity syndromes particularly obesity, diabetes and associated hypercorticoidism. The α-ET and/or β-ET are administered orally or parentally. The usual array of oral or parental dosage forms can be used, for example, tablets can be prepared by combining the α-ET and/or β-ET with the conventionally used binders and excipients. If desired, the compounds can be administered in a finely dispersed form, for example, as a finely dispersed powder or solution which is typically mixed with the food diet. In general, the administration amount to an average 70 kilo individual will be about 25 to 2,000 mg. per day and preferably about 50 to 400 mg. Unit dosage administration forms will generally contain about 25–1,000 mg., preferably about 50–400 mg., of the compounds. When combined with the diet, the compounds are usually used in an amount of up to about 1 percent by weight thereof. The compounds can be dissolved in a suitable solvent such as acetone, which is then mixed with food and thereafter the solvent is evaporated to leave the compounds in finely dispersed powdered form thoroughly mixed throughout the food.

The efficacy of α- and β-ET has been demonstrated in experiments with mice with diabetes-obesity condition produced by mutant diabetes (db) gene. The severity of the diabetes depends on the background genetic factors inherent in the inbred strains in which the mutations are maintained and expressed. The mice used were C57BL/Ks-db/db mice obtained from the Jackson Laboratory of Bar Harbor, Maine. In these mice, the diabetes mutation elicits an exaggerated obesity and a severe life-shortening diabetes. This diabetes is characterized by hyperplasia and hypertrophy of the beta cells of the islets of Langerhans, followed by severe degranulation and subsequent atrophy of the islets, rising blood glucose concentrations over 400 mg/dl, and death at 5–8 months.

Male mice were used. The mice were divided into groups, one of which was fed chow alone (Old Guilford 96) and others fed the chow into which either DHEA, α-ET or β-ET had been incorporated. Incorporation was effected by dissolving the compounds in acetone which was mixed with the food diet, followed by evaporation of the acetone prior to use.

The mice were weighed weekly at the time of bleeding for determination of the blood sugar concentration. Plasma immunoreactive insulin concentrations were quantified periodically during the treatment period and at the time of termination. After sacrifice, the pancreas was removed, weighed and one-half was fixed in Bouin's solution for subsequent histological study and morphometric analysis and the other half homogenized in acid-ethanol (1.5% concentrated HCl in 70% ethanol) to determine the pancreatic insulin content. Blood glucose, immunoreactive insulin (IRI) concentrations and glucose tolerance tests were carried out as described in Coleman, et al, Studies with the Mutation, Diabetes, in the Mouse, Diabetologia 3: 238-248 (1967).

Normal BL/Ks mice treated with α-ET or β-ET at concentrations up to 0.1% in the diet showed no toxic effects and food consumption was normal or slightly increased, whereas the rate of weight gain was slightly diminished. Blood sugar and plasma insulin concentrations remained within the normal range. Morphological analysis typically revealed 3 to 5 well-granulated islets in each section of the pancreases. The size, distribution and extent of beta cell granulation was not affected by the dietary treatments.

FIG. 1 shows the weight gain in the diabetes mutants treated for 18 weeks on chow alone (curve A), DHEA at 0.4% (curve B), α-ET at 0.1%, (curve C) and β-ET at 0.1% (curve D). As is apparent, both steroids decreased the rate of weight gain in the early stages of the disease when compared to the mutants which were fed chow only. The decrease in weight of the mutants fed chow only (curve A) after 16 weeks is indicative of the terminal decline in body weight. The mutants on all diets remained hyperphagic and food consumption was similar to that seen for the mutants fed chow alone.

FIG. 2 shows that α-ET and β-ET fed at a concentration of 0.1% were as effective as DHEA fed at 0.4% with respect to preventing the development of hyperglycemia.

The following Table I sets forth the effects of DHEA, α-ET and β-ET, and chow alone, on the diabetes syndrome in the mice which had been studied for 16 to 20 weeks after weaning, at which time they were sacrificed. In this table, the pancreatic insulin is given in standard insulin units per gram of pancreas wet weight and the granulated beta cells are given as a percent of islet area, i.e., as a percentage of the area of the islets of Langerhans. Each value set forth represents average values plus or minus the standard area of the mean for 4 to 8 individual mutant mice.

TABLE I

| Diet | Blood Sugar (mg/dl) | IRI (ul/ml) | Pancreatic Insulin (u/g) | Granulated-Cells (%) |
|---|---|---|---|---|
| Chow | 443 ± 30.1 | 99.6 ± 28.9 | 0.607 ± 0.16 | 4.05 ± 1.08 |
| DHEA (0.4%) | 156 ± 18.9 | 2374 ± 1883 | 10.4 ± 0.88 | 44.2 ± 6.18 |
| DHEA (0.1%) | 234 ± 36 | 1158 ± 178 | 4.60 ± 0.73 | 8.20 ± 1.50 |
| α-ET (0.1%) | 180 ± 23 | 251 ± 34 | 5.57 ± 0.72 | 22.6 ± 5.23 |
| β-ET (0.1%) | 148 ± 20.3 | 3141 ± 394 | 13.5 ± 0.55 | 15.3 ± 6.34 |

The beneficial effects observed in any treatment include reduction in blood sugar concentration and elevation in the pancreatic insulin content and in percent granulated beta cells as shown in Table I. Increased numbers of larger and reasonably well granulated islets are consistent findings in mutants treated with the steroids also shown in Table I. No signs of islet atrophy were ever observed.

The figures and Table I set forth above demonstrate that DHEA, α-ET and β-ET, were effective in preventing the development of severe diabetes in the BL/Ks diabetes mutants while having little effect on the amount of food eaten or the rate of weight gained. Obesity remained a constant feature of the treated mutants and no obvious signs of toxicity were observed. The α-ET and β-ET were fully effective at 0.1%, a concentration only ¼ the effective dose of DHEA (0.4%). This four-fold increased activity is significant. DHEA at 0.1% was not as effective as either α-ET or β-ET. Increased numbers of larger and reasonably well granulated islets were consistently found in the mice treated with a diet 0.1% by weight α-ET or β-ET but not with a diet 0.1% by weight DHEA. No signs of islet atrophy were observed with these treatments, whereas mice treated with 0.1% DHEA exhibited some atrophy with very little improvement in the extent of beta cell granulation. The treatment with α-ET or β-ET converted the severe diabetes symptoms to normal while having little effect on the obesity and residual insulin resistance.

The effects of these compounds, while beneficial, are reversible by cessation of administration of the compounds at least where the treatment has lasted up to 12 weeks. Furthermore, intervention with the treatment of the present invention has beneficial effects when introduced during any stage except the terminal stage of the diabetic cycle. The cycle is typically characterized by hyperactivity of the pancreas and hyperinsulinism followed by degeneration, then atrophy of the beta cells of the islet of Langerhans. Intervention at the early stages according to the present invention can actually avert the degeneration and atrophy, maintaining the islets in healthy condition despite continuing hyperactivity. Intervention at the later stages may reverse the process resulting in regeneration and enhancement of residual beta cell function.

In mutants carrying the mutation, (db/db) the most obvious effects seen with both DHEA and metabolites depend on the severity of the diabetes which depends on the inbred strain in which the mutant is maintained. Thus, metabolites in the C57BL/Ks mutant palliate the diabetes and have only a minor effect on rate of weight gain (see FIGS. 1 and 2). In contrast, diabetes mutants maintained on the C57BL/6 inbred background are characterized by a mild diabetes associated with severe obesity. On this strain, the beneficial effects of the metabolites involve, primarily, the rate of weight gain (FIG. 3 vs. FIG. 2). Even so, the decrease in weight gain observed, although significant, is not complete and the mutants still remain substantially obese, albeit free of diabetes symptoms.

The efficacy of α-ET and β-ET as anti-obesity agents is best demonstrated in other obese animal models which are less refractory to treatment with these steroids. The yellow ($A^{vy}$) mutation provides such a model that has a mild obesity syndrome with little diabetes and has been shown by others to be very responsive to DHEA treatment. Results of treatment of yellow mutants with either ET are shown in Table II which compares accumulated weight gain with time of treatment in these mutants fed either ET at 0.1%.

TABLE II

Effects of α- and β-ET on cumulative weight gain viable yellow ($\underline{A^{vy}/A}$) mutants.

| Treatment | Number and Sex | Average Cumulative Weight gain at | | |
|---|---|---|---|---|
| | | 4 wks | 8 wks | 12 wks |
| None | 7 males | 18.2 g | 26.7 g | 31.8 |
| DHEA (0.4%) | 8 males | 7.4 | 12.7 | 15.1 |
| α-ET (0.1%) | 3 males & 3 females | 7.4 | 10.1 | 16.3 |
| β-ET (0.1%) | 4 males & 3 females | 6.1 | 11.0 | 16.0 |

Treatments with either ET inhibited the rate of weight gain to about 50% of that seen in chow fed mutants. Note that each ET appears roughly 4 times as effective as DHEA. No androgenic or estrogenic hormonal side effects were observed and food consumption remained normal in all of these treatments. All mice regained excess body weight when returned to chow alone.

These results have been extended to treatments of mutant mice after their obesity has been established. In this study, $A^{vy}/A$ mutants 12 weeks of age were treated with either ET as shown in Table III.

TABLE III

Effects of α- and β-ET on established obesity in viable yellow ($A^{vy}/A$) mutants.

| Treatment[1] | Starting Weight g | Treatment Duration | | |
|---|---|---|---|---|
| | | 1 wk | 2 wks | 3 wks |
| α-ET (0.1%) | 45.3 ± 1.5 | 43.9 ± 1.7 (−1.6) | 43.2 ± 1.94 (−2.1) | 40.5 ± 1.6 (−4.8) |
| β-ET (0.1%) | 43.6 ± 0.45 | 42.7 ± 0.68 (−0.9) | 41.3 ± 0.57 (−2.3) | 39.9 ± 1.4 (−3.7) |

[1]Data based on average values from 3 male mice per treatment group.

Weight loss was more rapid depending on the degree of initial adiposity, being more rapid in the heavier animals and stopping at about the time the mutant had slimmed down to its normal fat free weight. The only tissue depleted was adipose tissue. No toxic effects were seen on prolonged treatment and food consumption remained unchanged in these groups. Weight gain resumed rapidly when treatment was withdrawn.

Another type of obesity to respond to treatment with either ET is the obesity that occurs naturally in certain strains with age. Aged normal (+/+) C57BL/6 male mice become moderately obese as do aged normal (+/+) littermates of mice carrying the viable yellow mutation. The effects of treatment with either ET (0.1%) in these aged normal mice is seen in Table IV.

TABLE IV

Effects of α- and β-ET on obesity associated with aged normal mice.

| Treatment[1] | Strain | Starting Weight g | Treatment Duration | | |
|---|---|---|---|---|---|
| | | | 1 wk | 2 wks | 4 wks |
| β-ET (0.1%) | BL/6 +/+ | 41.2 ± 2.3 | 39.3 ± 2.5 (−1.9 g) | 37.6 ± 2.7 (−3.6 g) | 37.8 ± 2. (−3.4 g) |
| α-ET (0.1%) | BL/6 +/+ | 53.9 ± 6.0 | 51.3 ± 5.8 (−1. g) | 46.7 ± 5.6 (−7.2 g) | 43.3 ± 4. (−10.6 g) |
| β-ET (0.1%) | C3H +/+ | 43.1 ± 1.2 | 39.5 ± 0.79 (−3.6 g) | 37.7 ± 0.81 (−5.4 g) | |
| α-ET (0.1%) | C3H +/+ | 42.2 ± 0.40 | 37.6 ± 0.69 (−4.6 g) | 36.1 ± 0.99 (−6.1 g) | |

Again, rapid weight loss continued during the early treatment period and slowed or stopped as the mice approached normal body weight. The group of normal BL/6 mice fed α-ET were initially substantially more obese than those fed β-ET and lost weight more rapidly.

These results clearly document the efficacy of α- and β-ET, with respect to their ability to treat diabetes, prevent obesity and control established obesity without any obvious detrimental consequences.

A typical capsule which can be prepared according to this invention will contain 50 mg. α-ET, 50 mg. lactose, 50 mg. dicalcium phosphate, 2 mg. magnesium stearate and 10 mg. of talc. Typical tablets can contain 50 mg. β-ET, 150 mg. starch, 5 mg. magnesium stearate, 10 mg. stearic acid and 40 mg. of dicalcium phosphate, or 50 mg. α-ET, 50 mg. β-ET, 150 mg. starch, 5 mg. magnesium stearate, 10 mg. stearic acid and 40 mg. of dicalcium phosphate.

A typical parental formulation is 10 mg of α-ET and 30 mg of glycine as sterile solids in an ampoule. Just before use, the ampoule contents are mixed with 3 ml of propylene glycol (or other diluent).

Various changes and modifications can be made in the method of the present invention without departing from the spirit and scope thereof. The various embodiments which have been described herein were for the purpose of further illustrating the invention but were not intended to limit it. Unless other otherwise specified, all temperatures are in degrees Centigrade and all parts and percentages are by weight throughout this specification and claims.

What is claimed is:

1. A method of treating a condition selected from the group consisting of obesity, diabetes syndromes, diabetes associated hypercorticoidism and combinations thereof which comprises administering to a mammal in need of such treatment an obesity, diabetes- or diabetes associated hypercortisolism-antagonistic effective amount of 5-β-androstan-3-ol-17-one.

2. The method of claim 1, wherein the administration is oral or parental.

3. The method of claim 2, wherein said compound is 5-β-androstan-3-α-ol-17-one.

4. The method of claim 2, wherein said compound is 5-β-androstan-3β-ol-17-one.

5. The method of claim 1, wherein the amount administered is about 25–2,000 mg. per 70 kilos per day.

6. The method of claim 5, wherein the amount is about 50–400 mg.

7. The method of claim 1, wherein said compound is administered in combination with food.

8. The method of claim 7, wherein said compound is present in an amount up to about 1% of said food.

9. The method of claim 7, wherein said compound is in finely dispersed powdered form.

10. The method of claim 1, wherein said compound is in finely dispersed powdered form.

11. The method of claim 1, wherein said compound is a mixture of 5-β-androstan-3α-ol-17-one and 5-β-androstan-3β-ol-17-one.

12. A method of treating obesity comprising administering to a mammal an obesity antagonistic effective amount of 5-β-androstan-3-ol-17-one.

13. The method of claim 12, wherein said compound is 5-β-androstan-3α-ol-17-one.

14. The method of claim 12, wherein said compound is 5-β-androstan-3β-ol-17-one.

15. The method of claim 12, wherein the amount administered is about 25–2,000 mg. per 70 kilos per day.

16. The method of claim 15, wherein the amount is 50–400 mg.

17. A composition for the treatment of a condition selected from the group consisting of obesity, diabetes syndromes, diabetes associated hypercorticoidism and combinations thereof comprising food having dispersed therein an obesity-, diabetes- or diabetes associated-hypercorticoidism antagonistic effective amount of 5-β-androstan-3-ol-17-one.

18. The composition of claim 17, wherein said compound is 5-β-androstan-3-α-ol-17-one.

19. The composition of claim 17, wherein said compound is 5-β-androstan-3β-ol-17-one.

20. The composition of claim 17, wherein said compound is present in an amount up to about 1% of said food.

21. A method of treating diabetes comprising administering to a mammal an obesity antagonistic effective amount of 5-β-androstan-3-ol-17-one.

22. The method of claim 21 wherein said compound is 5-β-androstan-3-α-ol-17-one.

23. The method of claim 21 wherein said compound is 5-β-androstan-3β-ol-17-one.

24. The method of claim 21 wherein the amount administered is about 25–2,000 mg/70 kilos per day.

25. The method of claim 24 wherein the amount is 50–400 mg.

* * * * *